(12) United States Patent
Weissenrieder et al.

(10) Patent No.: US 8,250,753 B2
(45) Date of Patent: Aug. 28, 2012

(54) METHOD FOR MANUFACTURING AN ACTIVE FIXATION ELECTRODE

(75) Inventors: Anna Norlin Weissenrieder, Stockholm (SE); Rolf Hill, Järfälla (SE); Olof Stegfeldt, Älta (SE); Marie Herstedt, Uppsala (SE); Mikael Forslund, Stockholm (SE); Susanne Nilsson, Huddinge (SE)

(73) Assignee: St. Jude Medical AB, Jarfalla (SE)

( * ) Notice: Subject to any disclaimer, the term of this patent is extended or adjusted under 35 U.S.C. 154(b) by 533 days.

(21) Appl. No.: 12/522,001

(22) PCT Filed: Jan. 31, 2007

(86) PCT No.: PCT/SE2007/000084
§ 371 (c)(1),
(2), (4) Date: Jul. 2, 2009

(87) PCT Pub. No.: WO2008/094081
PCT Pub. Date: Aug. 7, 2008

(65) Prior Publication Data
US 2010/0037457 A1 Feb. 18, 2010

(51) Int. Cl.
*H01R 43/00* (2006.01)

(52) U.S. Cl. .............. 29/872; 29/829; 29/606; 607/122; 600/461

(58) Field of Classification Search .............. 29/829, 29/868, 872, 606; 607/122, 127; 600/461–464, 600/467, 481, 508
See application file for complete search history.

(56) References Cited

U.S. PATENT DOCUMENTS

| 4,010,758 | A | 3/1977 | Rockland et al. |
| 4,026,303 | A | 5/1977 | Babotai |
| 5,324,322 | A | 6/1994 | Grill, Jr. et al. |
| 5,545,201 | A * | 8/1996 | Helland et al. ............... 607/127 |
| 5,689,877 | A * | 11/1997 | Grill et al. ..................... 29/825 |
| 6,501,994 | B1 | 12/2002 | Janke et al. |
| 2001/0000800 | A1 | 5/2001 | Partridge et al. |
| 2002/0072787 | A1 | 6/2002 | Partridge et al. |
| 2002/0188337 | A1 | 12/2002 | Bischoff |
| 2002/0188338 | A1 | 12/2002 | Bischoff |
| 2002/0188339 | A1 | 12/2002 | Bischoff et al. |
| 2002/0188340 | A1 | 12/2002 | Bischoff et al. |
| 2002/0193860 | A1 | 12/2002 | Bischoff et al. |
| 2003/0083727 | A1 | 5/2003 | Casavani et al. |
| 2003/0204232 | A1 | 10/2003 | Sommer et al. |
| 2005/0049665 | A1 | 3/2005 | Brabec et al. |
| 2006/0015164 | A1 | 1/2006 | Partridge et al. |
| 2006/0122682 | A1 | 6/2006 | Sommer et al. |

* cited by examiner

*Primary Examiner* — A. Dexter Tugbang
*Assistant Examiner* — Jeffrey T Carley

(57) ABSTRACT

In a method for manufacturing active fixation helices for the stimulation and/or sensing of organs, an elongated helix precursor body is produced that has one or more electrical conductors surrounded by an insulating material. This helix precursor body is then shaped into a helix, material removed in predetermined places in order to expose the areas of the conductors which will be used as electrodes in the final product. The body is coated with an electrically conducting biocompatible coating which is subsequently partly removed in continuous loops from around the electrodes in order to electrically insulate them from each other and to ensure that the electrically active areas of the electrodes are of the correct dimensions.

3 Claims, 6 Drawing Sheets

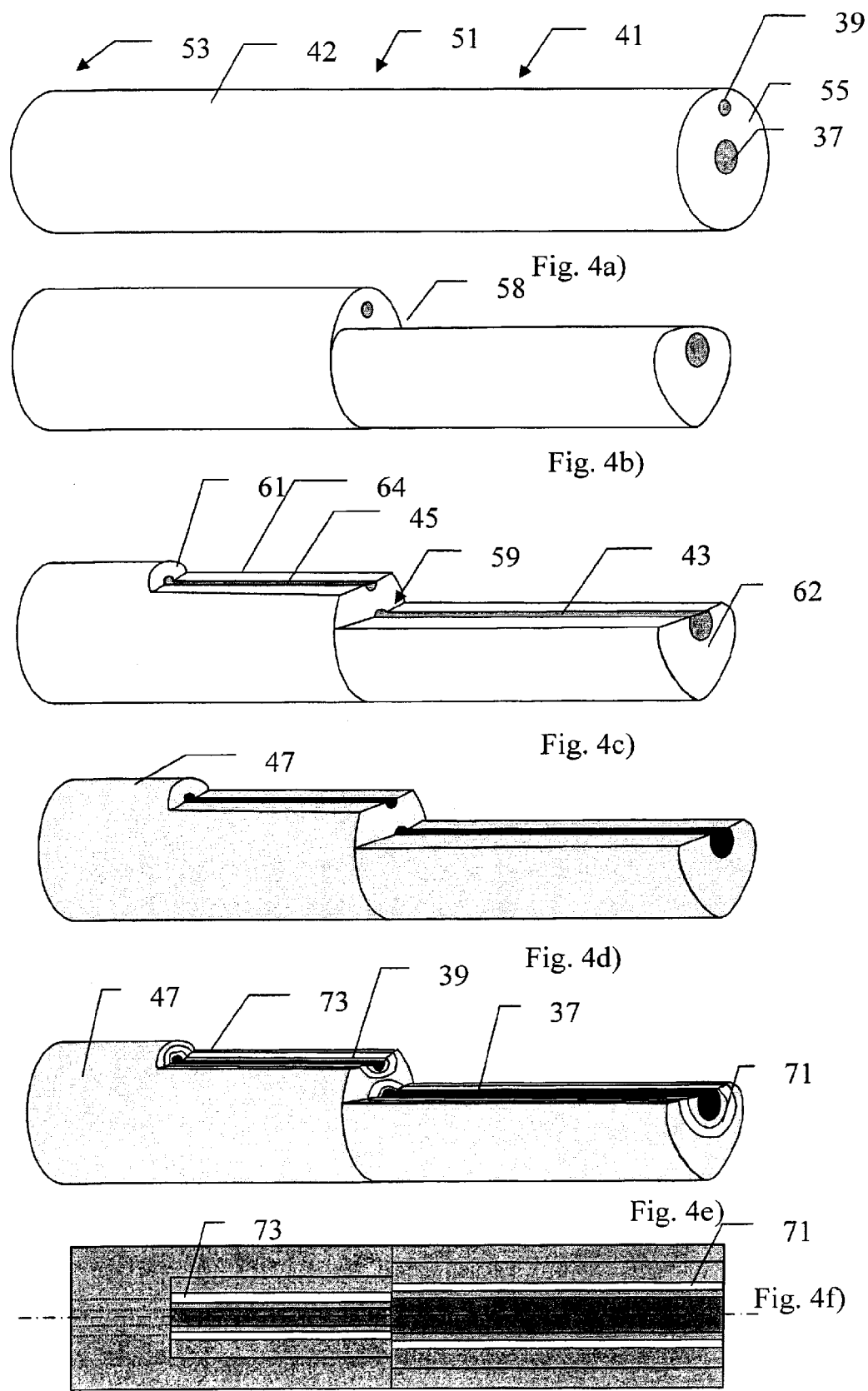

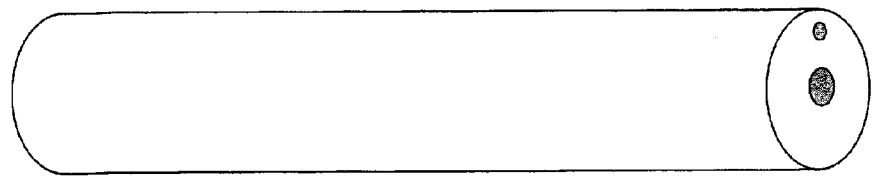
Fig. 5a)
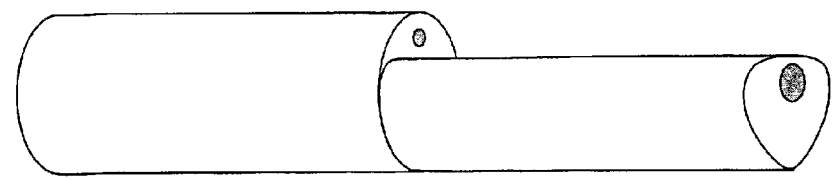
Fig. 5b)
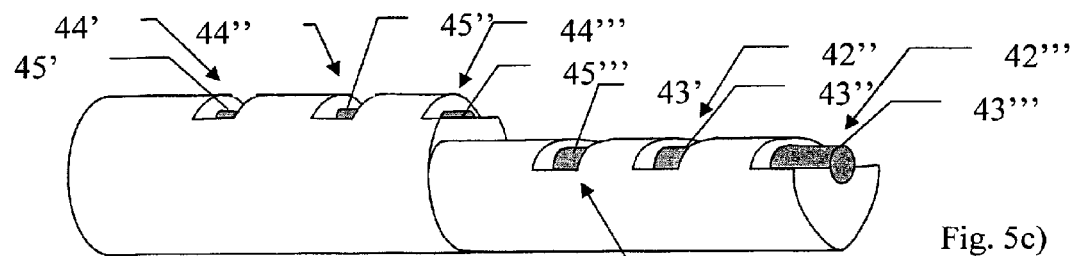
Fig. 5c)
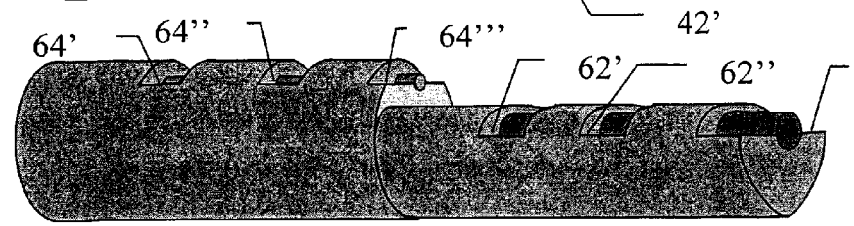
Fig. 5d)
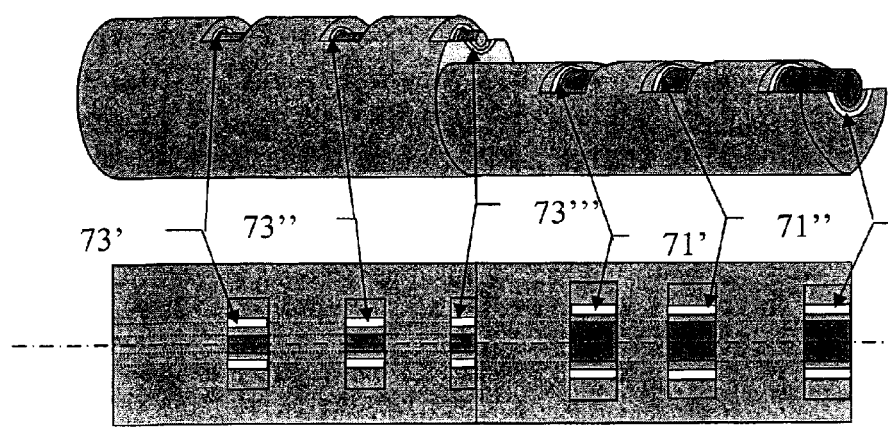
Fig. 5e)
Fig. 5f)

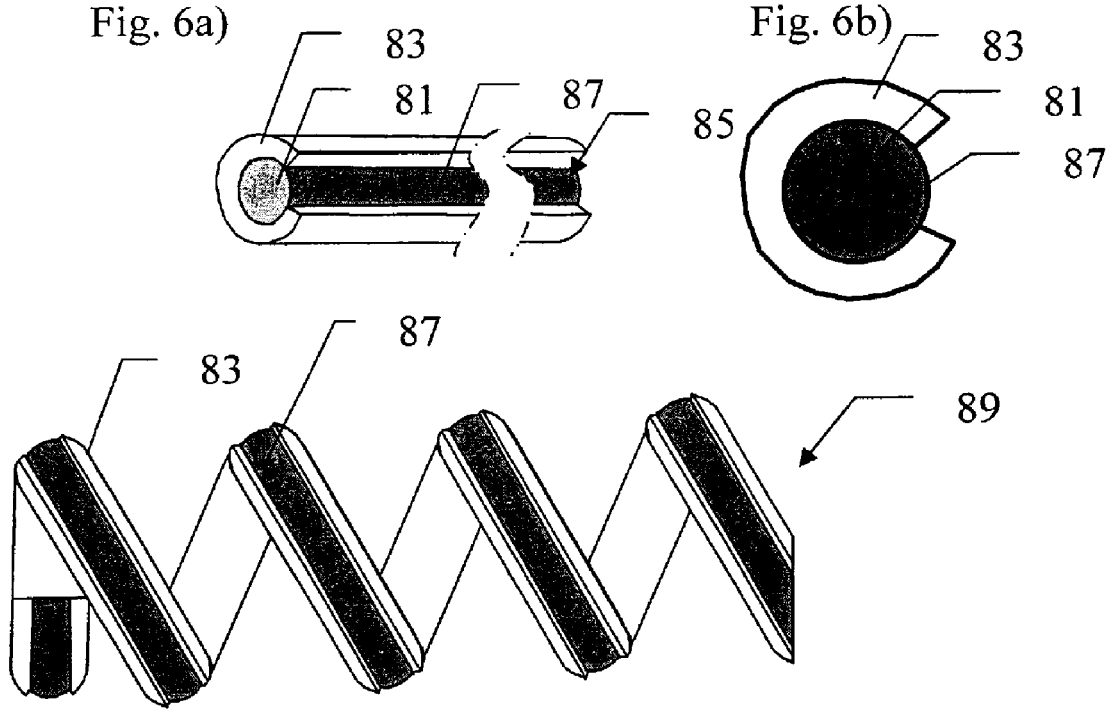
Fig. 6a)
Fig. 6b)
Fig. 6c)
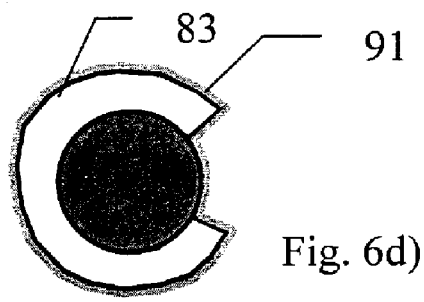
Fig. 6d)
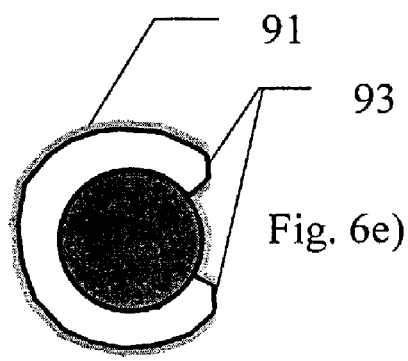
Fig. 6e)

METHOD FOR MANUFACTURING AN
ACTIVE FIXATION ELECTRODE

BACKGROUND OF THE INVENTION

1. Field of the Invention

The present invention relates to methods for manufacturing active fixation electrodes for electrical medical leads, in particularly helix electrodes intended to be screwed into body tissue.

2. Description of the Prior Art

Implantable medical electrical stimulation and/or sensing leads (also called "leads" or "electrode leads") are well known in the fields of tissue and organ stimulation and monitoring. Such fields include cardiac pacing. Leads may be attached to an organ by an active fixation means which is designed to penetrate the surface of the organ that is to be stimulated or sensed. A common active fixation means employs a helix which has a sharpened tip and is mounted at the end of the electrode lead. The fixation helix typically has an outside helix diameter which is slightly less than that of the lead body and extends in axial alignment with the lead body. The sharpened tip of the helix can be screwed into the organ by being rotated. Typically the helix is electrically connected to one or more conductors in the electrode lead. These conductors can be electrically connected to one or more exposed surfaces of the helix which then can be used as stimulating and/or sensing electrodes. A fixation helix therefore may contain one or a plurality of conductors. Typically the outer surface of the helix, including the exposed surfaces used as electrodes, is partly covered with a biocompatible coating to minimize interference with the tissue to which it is to be attached. Typically the biocompatible coating is electrically conducting and it is arranged in a predetermined pattern with continuous gaps on the insulating material und the exposed electrode surfaces in order to prevent the different electrodes from being in electrical contact with each other. The sizes of the surface areas of the exposed electrodes are set at levels which are compatible with the organ they are attached to United States Patent Application Publication 2006/0122682 describes an active fixation helix for an electrical medical leads and methods of making such active fixation helixes.

SUMMARY OF THE INVENTION

The present invention relates methods for manufacturing active helices suitable for use as active fixation electrodes for electrical medical leads, in particularly helix electrodes intended to be screwed into body tissue. Such helices are made of thin electrical conductors, encased in an insulating material—usually treated to be biocompatible, and twisted into the shape of a helix. The portions of the conductors are exposed to form electrically active surfaces which can be used for stimulating or sensing.

A first embodiment of a method in accordance with the present invention for making a helix includes a first step of producing an elongated helix precursor body having one or more electrical conductors surrounded by an insulating material. This helix precursor body is then shaped into a helix, material removed in predetermined places in order to expose the areas of the conductors which will be used as electrodes in the final product and coated with an electrically conducting biocompatible coating which is subsequently partly removed in continuous loops from around the electrodes in order to electrically insulate them from each other and to ensure that the electrically active areas of the electrodes are of the correct dimensions.

An alternative embodiment of a method in accordance with the present invention for making a helix comprises a first step of producing an elongated helix precursor body comprising one or more electrical conductors surrounded by an insulating material. Material is then removed at predetermined places from the helix precursor body in order to expose the areas of the conductors which will be used as electrodes in the final product. The body is coated with an electrically conducting biocompatible coating which is then removed in continuous loops from around the electrodes in order to electrically insulate them from each other and to ensure that the electrically active areas of the electrodes are of the correct dimensions. The body is then formed in to the shape of a helix.

BRIEF DESCRIPTION OF THE DRAWINGS

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

FIGS. 4a)-4f) show schematically steps in a first method in accordance with the present invention for making active fixation means.

FIGS. 5a-5f) show schematically stages in the manufacture of a multi-conductor helix precursor body.

FIGS. 6a)-6e) show schematically steps in a second method in accordance with the present invention for making an active fixation.

DESCRIPTION OF THE PREFERRED EMBODIMENTS

Figure 1:
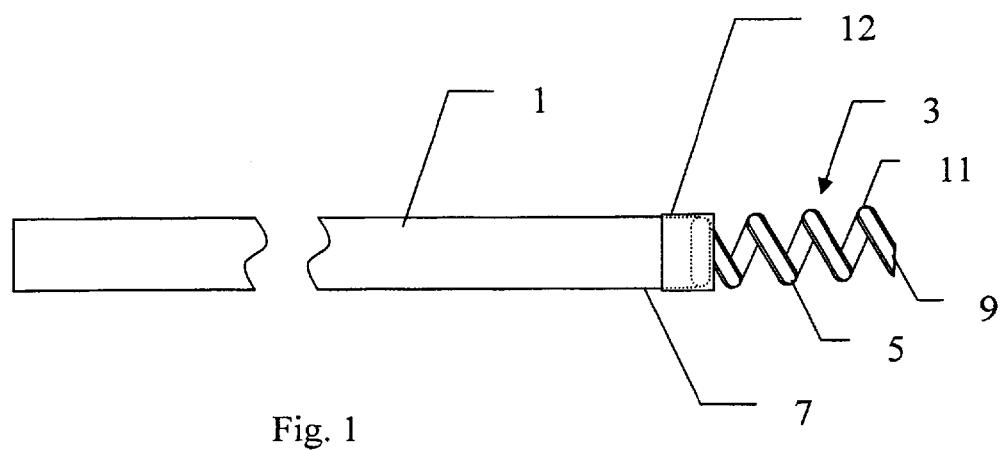
FIG. 1 shows schematically an example of an electrical medical lead provided with active fixation.

FIG. 1 shows schematically an example of an electrical medical lead 1 provided with an active fixation means 3. The active fixation means is formed by an electrically active helix 5 having a proximal end 7 in electrical connection with a conductor (not shown) inside said electrical medical lead 1 and a sharpened distal end 9. A number of helix revolutions 11 are arranged between said proximal end 7 and said distal end 9. The helix 5 is attached to the lead 1 by a sleeve 12 which surrounds the end of the lead and one or more revolutions 11 of the helix 5.

Figure 2:
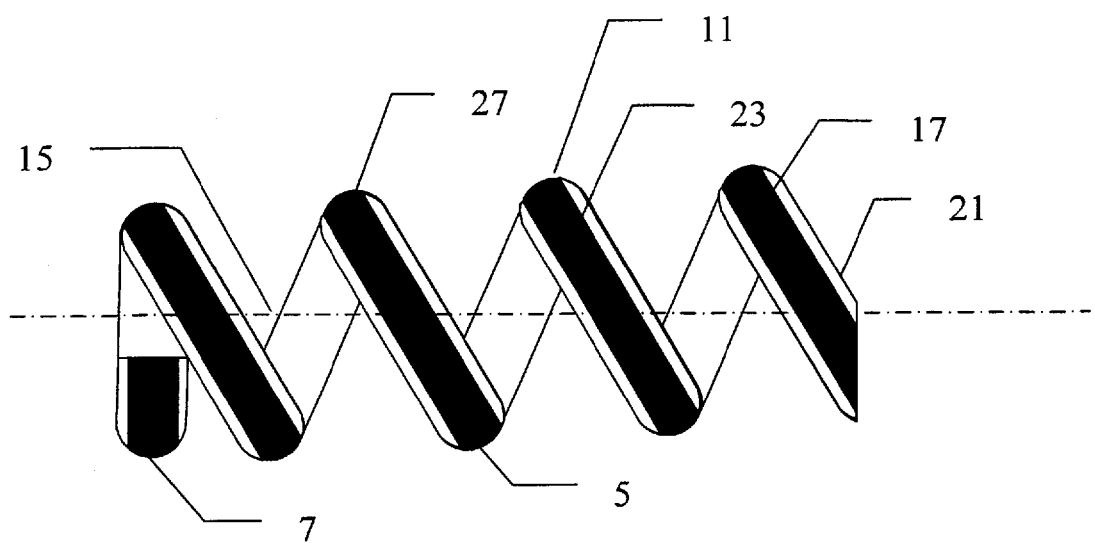
FIG. 2 shows schematically an embodiment of electrically active helix having a single conductor.

FIG. 2 shows schematically an embodiment of electrically active helix having a single conductor. The helix body 13 surrounds a longitudinally extending lumen 15 and is comprised of an electrically conducting core 17 which is at least partially surrounded by an insulating sheath 21 such that a continuous portion of the surface 23 said electrically conducting core 17 is exposed. The exposed surface 23 is coated with an electrically conducting biocompatible coating 27 and preferably the insulating sheath is also covered with a biocompatible coating. In order to electrically insulate the exposed surface 23 of the core 17 from the rest of the surface of the helix body, a continuous loop of the surface of the helix surrounding said exposed surface 17 must be free of electrically conducting material.

Figure 3:
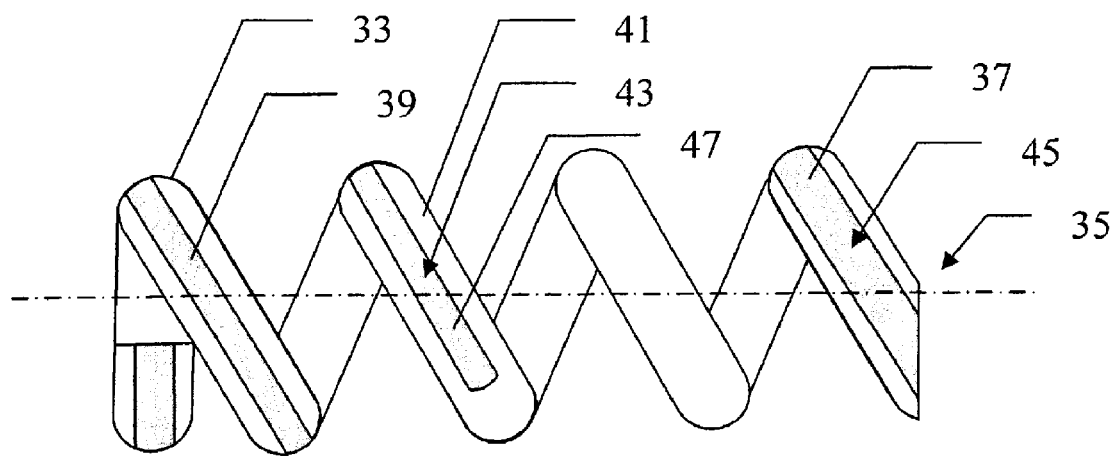
FIG. 3 shows schematically an embodiment of a multi-conductor electrically active helix.

FIG. 3 shows schematically an embodiment of a multi-conductor electrically active helix. The helix body 33 surrounds a longitudinally extending lumen 35 and is comprised of electrically conducting cores 37, 39 each of which is at least partially surrounded by an insulating sheath 41 such that a continuous portion of the surface 43, respectively 45, of each the electrically conducting cores 37, 39 is exposed. Each exposed surface 43, 45 of the cores and the insulating sheath 41 is coated with an electrically conducting biocompatible coating 47 but the exposed surfaces 43, 45 are electrically insulated from each other and the sheath 41 by being surrounded by a continuous loop of insulating material. This is described in more detail below.

A first embodiment of a method for producing an active fixation means in the form of a multi-conductor electrically active helix will now be described in connection with FIGS. 4a)-4e). In a first step an elongated cylindrical helix body precursor 51 is formed. This helix body precursor 51 has a proximal end 53 and a distal end 55 and comprises first and second elongated electrically conducting cores 37, and 39, surrounded by a sheath 41 of insulating material 42. The cores 37, 39 can be made of any suitable conducting material, for example a metal such as platinum.

An example of such a helix body precursor 51 is shown in FIG. 4a). In this example the first core 37 is arranged along the central longitudinal axis of the helix body precursor 51 and the second core 39 is arranged parallel to the first core 37 and between the first core 37 and the outer surface 57 of the helix body precursor. This can be achieved for example by co-extruding the cores 37, 39 inside an insulating sheath material.

In the next step of the method a predetermined length of second core 39 and the insulating material surrounding it are removed from distal end 55, leaving a shoulder 58 in the helix body precursor 51, said shoulder extending over a portion of the first core 37 which is still surrounded by insulating material 42 as shown in FIG. 4b).

In a third step, as shown in FIG. 4c) shoulders 59, resp. 61, are formed in the insulating sheath 41 by selectively removing insulating material from the distal end 55 of the helix body precursor 51 in order to expose resp. a surface 43 of the first electrically conducting core 37, and a surface 45 of the second electrically conducting core 39. In this example shoulder 59 is a continuation of shoulder 58 in a direction towards the first electrically conducting core 37 but it is possible to place shoulder 59 further away from the distal end 55 than shoulder 58, thereby removing or undercutting shoulder 58. In this embodiment of the present invention part of exposed first core 37 nearest the distal end 55 of the helix body precursor 51 is leveled so that the exposed surface 43 is coplanar with the longitudinally extending surface 62 of shoulder 59. Similarly part of exposed second core 39 nearest the distal end 55 of the helix body precursor 51 is removed so that its exposed surface 45 is coplanar with the longitudinally extending surface 64 of shoulder 61. As alternatives one or more of the exposed surfaces of the cores can be left standing proud of the surrounding longitudinally extending surface e.g. with a convex exposed surface, or, conversely, one or more exposed cores surfaces can be sunk into the surrounding longitudinally extending surface, e.g. with a concave exposed surface. While this step has been described as following the preceding step it is of course possible to perform these two steps substantially simultaneously.

Subsequently, as shown in FIG. 4d) a continuous electrically conducting biocompatible coating 47 can be applied to the exposed surface of said helix body precursor so that it covers the insulating sheath, shoulders 59, 61 and the exposed surfaces 43, 45 of the electrically conducting cores 37, 39.

Finally, as shown in FIGS. 4e) and 4f) a continuous loop 71, resp. 73 of said electrically conducting biocompatible coating 47 on the insulating sheath surrounding each of the exposed surfaces 43, 45 of the electrically conducting cores 37, 39 is removed. The result of this is that each electrically conducting coating on the exposed surface 43, 45 of each core 37, 39 is not in electrical contact with the remaining electrically conducting coating 47 on the insulating sheath. This limits the electrically-effective surface area of each exposed core surface which will subsequently be used as sensing or stimulating electrodes. The biocompatible coating can be removed by, for example, cutting, polishing, grinding or similar methods. The elongated helix body precursor can now be formed into a helical shape comprising an internal lumen by winding around a cylindrical former or by any other known way in order to form a helix body comprising a number of revolutions separating a distal end and a proximal end. Preferably the forming of the helical shape is performed so that the exposed surface of each core is orientated in a predetermined direction, for example toward the exterior of the helix. As in this embodiment of the present invention the forming of the helix revolutions takes place after the electrically conducting biocompatible coating has been applied to the insulating sheath, it is preferable that the bonding of the biocompatible coating to the underlying sheath and exposed surface of the electrically conducting core is sufficiently strong that the biocompatible coating is not disturbed or moved during forming of these revolutions. Examples of coatings which exhibit such strong bonding are titanium oxide, platinum black, and metal oxides formed from the conducting wire or lead.

FIGS. 5a)-5f) show stages in the manufacture of a multi-conductor electrically active helix in which each conductor has a number of active electrode in accordance with the above first embodiment of a method for producing active fixation. In these figures the reference numerals used in FIGS. 4a)-4f) have been repeated when they correspond to similar features. As can be seen from FIGS. 5a)-5f) the stages in this method are substantially the same as those described above except that in the third step, as shown in FIG. 5c), a number of cuts are made in the insulating sheath and insulating material removed from between alternating pairs of cuts in order to form slits 42', 42", 42"' and 44', 44", 44"' which expose a number of longitudinally extending surfaces 43', 43", 43"' of the first electrically conducting core 37, and a number of longitudinally extending surfaces 45', 45", 45"' of the second electrically conducting core 39. In this embodiment of the present invention exposed portions of first core 37 nearest the distal end 55 of the helix body precursor 51 are not levelled, i.e. the exposed surfaces 43', 43", 43"' project above the longitudinally extending surfaces 62 of the slits 42', 42", 42"' formed in shoulder 59. Similarly the exposed portions of second core 39 nearest the distal end 55 of the helix body precursor 51 are not levelled, i.e. the surfaces of its exposed surfaces 45', 45", 45"' project above the longitudinally extending surfaces 64 of the slits 44', 44", 44"' formed in shoulder 61. As alternatives one or more of the exposed surfaces 43'-43"', 45'-45"' of the cores can made level with the surrounding longitudinally extending slit's surface or, one or more exposed cores surfaces can be sunk into the surrounding longitudinally extending slit's surface, e.g. with a concave exposed surface. While this step has been described as following the preceding step it is of course possible to perform these two steps substantially simultaneously.

Subsequently, as shown in FIG. 5d) a continuous electrically conducting biocompatible coating 47 can be applied to the exposed surface of said helix body precursor so that it covers the insulating sheath, shoulders 59, 61 and the exposed surfaces 43'-43''', 45'-45''' of the electrically conducting cores 37, 39.

Finally, as shown in FIGS. 5e) and 5f) a continuous loop 71'-71''', resp. 73'-73''' of said electrically conducting biocompatible coating 47 on the insulating sheath surrounding each of the exposed surfaces 43'-43''', 45'-45''' of the electrically conducting cores 37, 39 is removed. The result of this is that each electrically conducting coating on the exposed surfaces of each core 37, 39 is not in electrical contact with the remaining electrically conducting coating 47 on the insulating sheath. This limits the electrically-effective surface area of each exposed core surface which will subsequently be used as sensing or stimulating electrodes. The biocompatible coating can be removed by, for example, cutting, polishing, grinding or similar methods. The elongated helix body precursor can now be formed into a helical shape having an internal lumen by winding around a cylindrical former or by any other known way in order to form a helix body comprising a number of revolutions separating a distal end and a proximal end. Preferably the forming of the helical shape is performed so that the exposed surface of each core is orientated in a predetermined direction, for example towards the exterior of the helix.

In a second embodiment of a method for producing an active fixation in the form of an electrically active helix, the helix body precursor is formed into a helical shape before the surfaces of the conducting core or cores are exposed. Thus this method is similar to the first embodiment of the invention except that the forming of the helix is performed before the application of coatings. In more detail an example of a second embodiment of the present invention includes the steps of:

a) forming a helix body having a proximal end and a distal end connected by a number of helical revolutions, said body comprising at least one electrically conducting core partially surrounded by an insulating sheath whereby a continuous portion of the surface of each electrically conducting core extending from the distal end toward the proximal end and facing in a predetermined direction is exposed;

b) applying a continuous electrically conducting, biocompatible coating to surface of the insulating sheath and each exposed surface of each electrically conducting core;

c) removing a portion of the electrically conducting biocompatible coating on the insulating sheath surrounding each continuous portion of the surface of each electrically conducting core such that the electrically conducting coating on the exposed surface of each electrically conducting core is not in electrical contact with the remaining electrically conducting coating on the insulating sheath.

In the above examples, the exposed surfaces 43-45''', and 45-45''' which are to act as sensing or stimulating electrodes, are quadratic when seen from a view perpendicular to the exposed surface and extend longitudinally, but it is possible for them to made in any shape.

There are several possible ways of forming an elongated helix body precursor. For example, as shown in FIGS. 6a) and 6b) a electrically conducting core 81 and an insulating sheath 83 can be extruded simultaneously, the insulating sheath 83 being formed with a longitudinal slit 85 such that a continuous longitudinally extended portion of the surface 87 of the electrically conducting core 81 is exposed and not surrounded by the insulating sheath 83.

Such an elongated helix body precursor can be formed into a helix 89 as shown in FIG. 6c), for example by winding around a former. The complete helix 89 can then be coated with a biocompatible conductive material 91 such as titanium nitride by, for example, vapor deposition as shown in FIG. 6d). In order to isolate the exposed surface 87 of the core 81 which is intended to be electrically active during use from the surface of the insulating sheath 83 which is intended to be inactive during use, continuous strips 93 of the biocompatible conductive material 91 on the insulating sheath 83 can be removed, by polishing, cutting or other suitable methods, leaving a continuous non-conducting gap 93 between the core 85 and the major part of the visible surface of the insulating sheath, as can be seen in FIG. 6e).

Figure 7A:
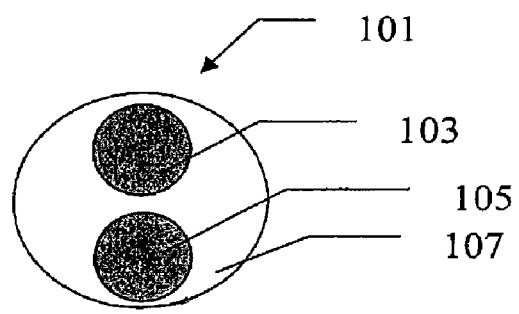
FIGS. 7a)-7c) show schematically cross-sections through examples of possible helix precursor bodies.

FIGS. 7a)-7c) show schematically examples of further possible helix body precursors in cross-section. FIG. 7a) shows a cross-section through a co-extruded or co-formed precursor body 101 containing two symmetrically-positioned conducting cores 103, 105 of circular cross-section surrounded by a circular insulating sheath 107.

Figure 7B:
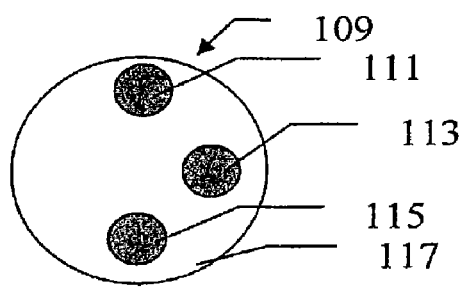

FIG. 7b) shows a cross-section through a co-extruded or co-formed precursor body 109 containing three conducting cores 111, 113, 115 each of circular cross-section surrounded by a circular insulating sheath 117. The cores are arranged with the two cores positioned at 90° either side of a middle core—thereby leaving a gap of approximately 180° of insulating material without any cores. Preferably this gap is arranged to be facing towards the interior of the helix when the precursor is formed into a helix.

Figure 7C:
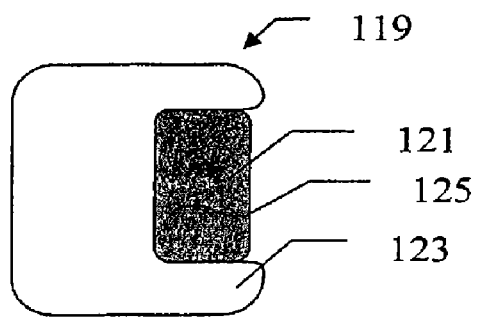

FIG. 7c) shows a cross-section through a co-extruded or co-formed precursor body 119 containing an asymmetrically-positioned core 121 of quadratic cross-section positioned inside an insulating sheath 125 of C-shaped cross-section, with a surface 125 of core 121 exposed.

The above suggested cross-sections are merely examples of conceivable cross-sections—the skilled person would understand that in the event that a lead, precursor body or helix has a plurality of conductors it is always possible to remove selectively insulating material in predetermined positions so that when in use in a patient conductors can come into contact with tissue and thereby be used as a stimulating and/or sensing electrode.

Although modifications and changes may be suggested by those skilled in the art, it is the intention of the inventors to embody within the patent warranted heron all changes and modifications as reasonably and properly come within the scope of their contribution to the art.

We claim as our invention:

1. A method of fabricating an electrically active helix for an electrical medical lead comprising:

a) forming an elongated helix body precursor having a proximal end and a distal end, the helix body precursor comprising at least one electrically conducting core surrounded by an insulating sheath;

b) removing a predetermined length of the insulating sheath such that a portion of a surface of each electrically conductive core between the distal end and the proximal end is exposed;

c) applying a continuous electrically conducting, biocompatible coating to the longitudinally-extending surface of the insulating sheath and each exposed surface of each electrically conducting core;

d) removing a portion of the biocompatible coating on the insulating sheath to form a biocompatible coating free window surrounding each continuous portion of the surface of each electrically conducting core such that each biocompatible coating on the exposed surface of each electrically conducting core is not in electrical contact with the remaining biocompatible coating on the insulating sheath; and e) forming the helix body precursor into a helix body in which a plurality of helical revolutions are formed between the proximal end and the distal end of the helix body precursor, and wherein each exposed surface of each electrically conducting core faces in a predetermined direction.

2. The method of claim 1 comprising, in step d) removing the portion of electrically conducting biocompatible coating by polishing or cutting or grinding or a combination thereof.

3. The method of claim 1 wherein the biocompatible coating is selected from a group consisting of TiN or TiSiC or platinum black or a metal oxide or other electrically conducting material.

* * * * *